US006577886B1

(12) United States Patent
Takaoka et al.

(10) Patent No.: US 6,577,886 B1
(45) Date of Patent: Jun. 10, 2003

(54) LIVING BODY FUNCTION MEASUREMENT METHOD

(75) Inventors: Hideyuki Takaoka, Sapporo (JP); Uma Maheswari Rajagopalan, Tokorozawa (JP); Manabu Tanifuji, Asaka (JP); Tomio Endo, Hidaka (JP)

(73) Assignees: Olympus Optical Co., Ltd., Tokyo (JP); Riken, Wako (JP)

( * ) Notice: Subject to any disclaimer, the term of this patent is extended or adjusted under 35 U.S.C. 154(b) by 104 days.

(21) Appl. No.: 09/930,416

(22) Filed: Aug. 15, 2001

(51) Int. Cl.[7] .................................................. A61B 5/05
(52) U.S. Cl. ........................ 600/407; 600/476; 356/484
(58) Field of Search ................................. 600/407, 476; 356/484, 497, 479

(56) References Cited

U.S. PATENT DOCUMENTS

| 5,321,501 | A | | 6/1994 | Swanson et al. | |
|---|---|---|---|---|---|
| 6,151,127 | A | * | 11/2000 | Kempe | 356/484 |
| 6,381,023 | B1 | * | 4/2002 | Kempe | 356/484 |

FOREIGN PATENT DOCUMENTS

| JP | 2890309 B2 | 2/1999 |
|---|---|---|

OTHER PUBLICATIONS

David Huang et al; Optical Coherence Tomography; Science, vol. 254; Nov. 1991; pp. 1178–1180.
Tobias Bonhoeffer et al; Optical Imaging Based on Intrinsic Signals; The Methodology; copyright 1996 by Academic Press, Inc. pp. 55–97.
Tobias Bonhoeffer et al; The Layout of Iso–orientation Domains in Area 18 of Cat Visual Cortex: Optical Imaging Reveals a Pinwheel–like Organization; Oct. 1993; The Journal of Neuroscience, 13 (10) ; pp. 4157–4180.

* cited by examiner

Primary Examiner—Marvin M. Lateef
Assistant Examiner—Runa Shah Qaderi
(74) Attorney, Agent, or Firm—Frishauf, Holtz, Goodman & Chick, P.C.

(57) ABSTRACT

A living body function measurement method comprises separating a light from a low coherence light source into a signal light and a reference light, modulating a frequency of at least one of the signal light and the reference light, irradiating the signal light to an observation area of a living body sample, giving a stimulation to the living body sample from an outside of the living body sample, synthesizing the signal light via the observation area and the reference light and detecting a heterodyne interference signal, and measuring a living body function of the observation area by measuring a change in the heterodyne interference signal when the stimulation is changed.

17 Claims, 3 Drawing Sheets

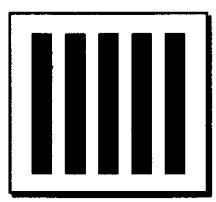
F I G. 4A
F I G. 4B
F I G. 5A
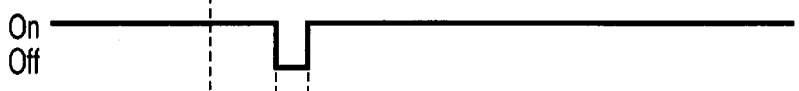
F I G. 5B
F I G. 5C
F I G. 5D
F I G. 5E
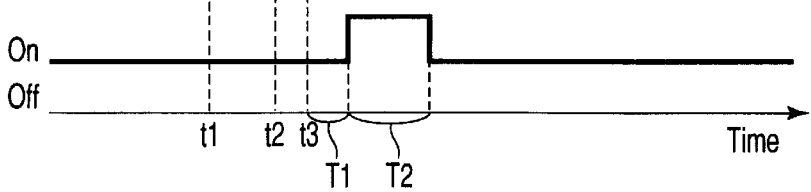
F I G. 5F
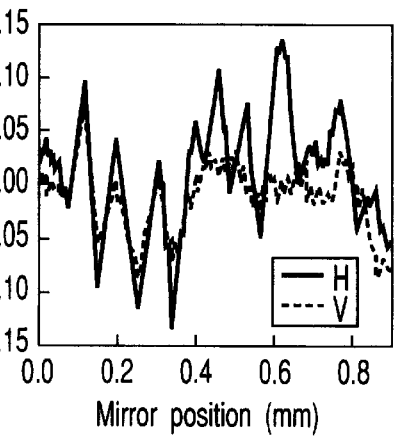
F I G. 6

LIVING BODY FUNCTION MEASUREMENT METHOD

BACKGROUND OF THE INVENTION

1. Field of the Invention

The present invention relates toll a living body function measurement method to observe various reactions when certain kinds of stimulations are given to a living body.

2. Description of the Related Art

The living body function measurement method is a method of observing various reactions when certain kinds of stimulations are given to the living body. Especially, the neural activity following the stimulation given to the sensory organ etc. is observed in the measurement of the brain function. That is, the following living body reactions are occurred along with the neural activity.

(1) Change in an amount of the reduced hemoglobin.
(2) Change in blood flow.
(3) Change in thickness of blood vessel.
(4) Structural changes in cell in organization.

The function in the observation portions of the brain is measured by observing these reactions.

A method of observing these reactions by using the light is well known. Especially, a technique of measuring a brain function is disclosed in T. Bonhoeffer and A. Grinvald, "Optical Imaging Based on Intrinsic Signals In Brain Mapping the Methods", Academic Press Inc. (1996), or Bonhoeffer, A. Grinvald, "The layout of Iso-orientation domains in Area 18 of cat visual cortex: Optical Imaging reveals a Pinwheel-like Organization", J. Neurosci. 13, 4157–4180 (1993), etc. Each of these techniques is a technique of irradiating a visible light to the exposed brain, and measuring the reflected light intensity distribution on the surface of the brain as a change of stimulation.

On the other hand, the device, which measures the function of the scatterer sample of the living body etc., is disclosed in the Japanese Patent No. 2890309. In this device, the light is irradiated to the scatterer sample, and the heterodyne of the, transmitting light is detected.

However, since the living body is a scatterer, generally, when the function in the living body is measured by using the light, the reflected light from the observation point in the living body becomes very weak. Therefore, it is very difficult to perform the function measurement of the living body at deeper position than the surface to be observed.

An OCT (Optical Coherence Tomography) is known as a technique which observes the structure in the scatterer of the living body etc. (see U.S. Pat. No. 5,321,501). The example of observing the structure in the living body by using the technique of this OCT is described in SCIENCE, VOL. 254, P1178 (1991), etc. In the OCT, the structure in the sample can be observed with high depth resolution by the heterodyne detection by using the light source with low coherence. The depth resolution is almost equal to the coherence length of the light source to be used. On the other hand, in the technique disclosed in the patent above-mentioned No. 2890309, the heterodyne detection is used. However, it is difficult to obtain the high depth resolution since a use of the low coherence light is not shown. Since the technique is la method to detect the transmitting light of the sample, it is difficult to observe an especially big sample and animal sample.

BRIEF SUMMARY OF THE INVENTION

An object of the present invention is to provide a technique, which performs a living body function measurement in the living body with high-resolution evaluation.

A living body function measurement method according to the present invention is characterized by comprising: separating a light from allow coherence light source into a signal light and al reference light; modulating a frequency of at least one of the signal light and the reference light; irradiating the signal light to an observation area of a living body sample; giving a stimulation to the living body sample from an outside of the living body sample; synthesizing the signal light via the observation area and the reference light and detecting a heterodyne interference signal; and measuring a living body function of the observation area by measuring a change in the heterodyne interference signal when the stimulation is changed.

BRIEF DESCRIPTION OF THE SEVERAL VIEWS OF THE DRAWING

FIG. 4A and FIG. 4B are figures, which show spatial patterns becoming a visual stimulation in the second example;

FIGS. 5A to 5F are figures, which show an operation timing of each equipment connected with a synchronous circuit; and FIG. 6 is a figure, which shows an observation result in the second example.

DETAILED DESCRIPTION OF THE INVENTION

Figure 1:
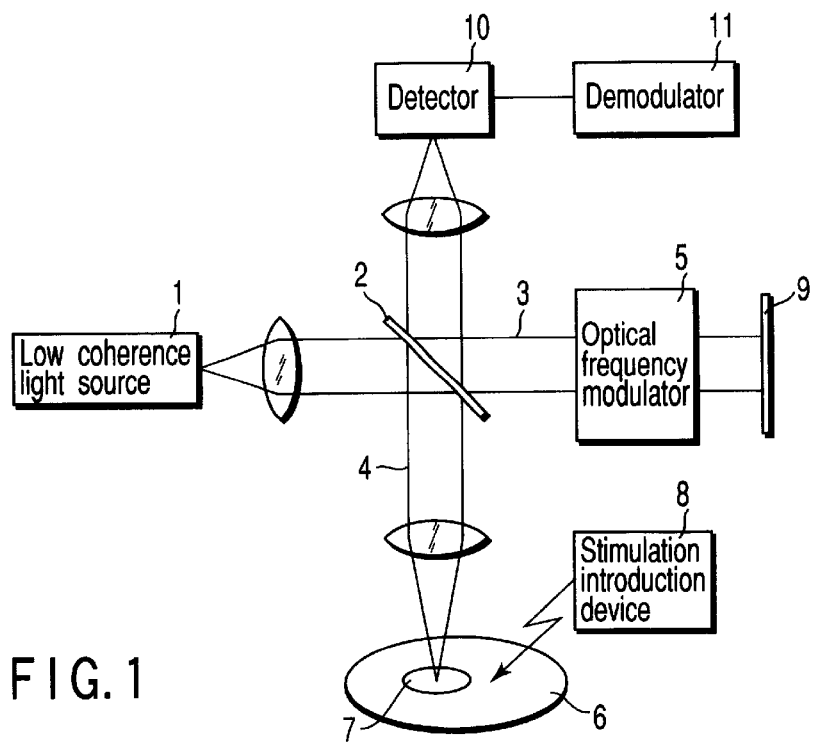
FIG. 1 is a figure, which shows an outline configuration of a living body function measurement method according to an embodiment of the present invention.

Hereinafter, an embodiment of the present invention will be explained referring to the drawings. FIG. 1 is a figure, which shows an outline configuration to explain the living body function measurement method according to an embodiment of the present invention.

A light emitted from a low coherence light source 1 is separated into a reference light 3 and a signal light 4 by a coupler 2. The optical frequency of the reference light 3 is modulated by an optical frequency modulator 5. The signal light 4 is irradiated to an observation area 7 of a living body sample 6. A stimulation introduction device 8 gives a stimulation to the living body sample 6.

The signal light 4 passing through the observation area 7 and the reference light 3 reflected by a mirror 9 are synthesized by the coupler 2 and are detected with a detector 10. A demodulator 11 demodulates the signal detected with the detector 10 by the frequency corresponding to the modulation frequency of the optical frequency modulator 5 and is output as a heterodyne interference signal.

The intensity of the heterodyne interference signal output from the demodulator 11 also changes, when an optical characteristic of the observation area 7 changes by the reaction introduced into the living body sample 6 by the stimulation introduction device 8 and the observation area 7 does some reactions by the stimulation. The reaction of the observation area 7 to stimulation can be observed by the change in the intensity of the heterodyne interference signal. The optical characteristic is a parameter such as the reflectivity of light, the characteristic of scattering, and the absorption characteristic, etc. which may influence upon the signal light.

As described above, since the low coherence light source 1 is used in this embodiment, the interference signal is detected only when the length of the optical path of the signal light 4 and the reference light 3 thereof are almost coincide. Therefore, the information in the living body sample is observed by the depth resolution of the coherence length level of the low coherence light source 1. The information in the living body sample which is the scatterer can be detected with high sensitivity by detecting the heterodyne.

The difference of the intensity of the heterodyne interference signal is measured before and after changing the stimulation in the embodiment. That is, the output signal of the demodulator 11 is introduced into the arithmetic unit, and the difference of each value before and after introducing the stimulation by the stimulation introduction device 8 is measured with the arithmetic unit. The presence of the reaction by stimulation is judged by this measurement result. The largeness of the reaction by stimulation is relatively measured by the amount of the arithmetic result.

FIRST EXAMPLE

Figure 2:
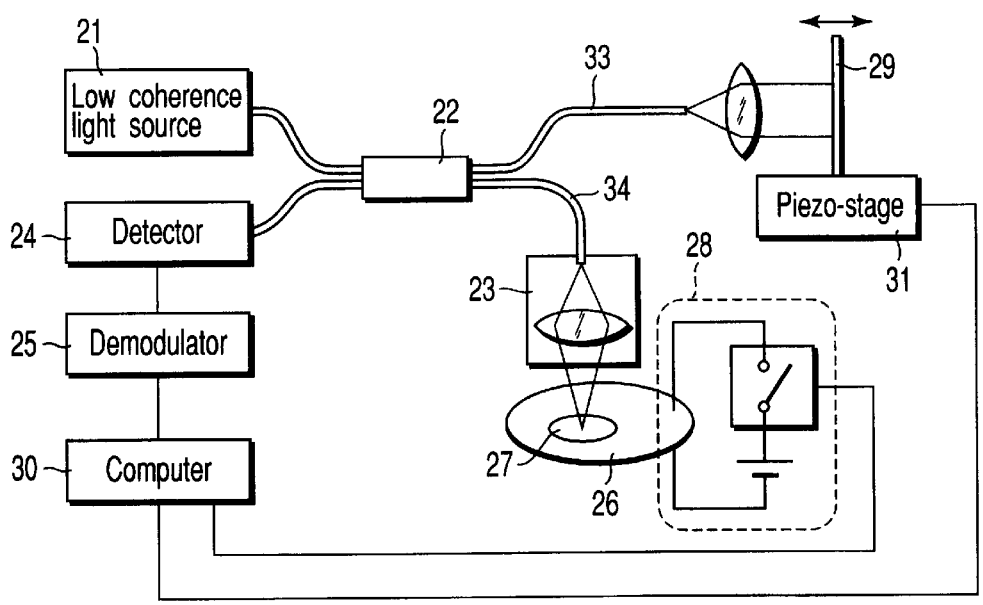
FIG. 2 is a figure, which shows a configuration to achieve a measurement method according to the first example of the present invention.

The first example of the living body function measurement method according to the present invention will be explained referring to FIG. 2. For example, the light emitted from the low coherence light source 21 such as SLD (SuperLuminecent Diode) is led to the fiber coupler 22 through the optical fiber, and separated into the reference optical path 33 and the signal optical path 34 by the fiber coupler 22. The light of the reference optical path 33 is reflected with the mirror 29 arranged on the piezo-stage 31 and returns to the fiber coupler 22. The light of the signal optical path 34 is irradiated to the observation area 27 of the living body sample 26 by the probe optical system 23. The reflected light from the observation area 27 returns to the fiber coupler 22.

The reflected light from the mirror 29 and the reflected light from the living body sample 26 are synthesized by the fiber coupler 22 and are detected with the detector 24. An output of the detector 24 is input to the demodulator 25 and is demodulated by the demodulator 25. The output signal of the demodulator 25 is input to the computer 30.

The mirror 29 reciprocates by reciprocating the piezo-stage 31 in a constant distance, and the frequency of the light reflected by the mirror 29 receives Doppler shift. The demodulator 25 demodulates the signal by a corresponding frequency to the Doppler shift frequency.

The electric stimulation is given to the living body sample 26 with the electric stimulation introduction device 28. Turning-on and -off of the electric stimulation are controlled by, the computer 30. The computer 30 synchronously performs the control of the electric stimulation introduction device 28 and control of taking of the output signal of the demodulator 25. The computer 30 records the output signal from the demodulator 25 in each of an on-state and an off-state of the electric stimulation in the electric stimulation introduction device 28, and calculates and outputs the difference of the value of the output signal.

The presence of the reaction or largeness thereof can be observed in the observation area in the living body sample, when the electric stimulation is introduced into the living body sample by the living body function measurement method of this example.

The reaction when a medicine and a chemical material, etc. are administered to the living body sample can be checked in, for example, as the stimulation given to the living body sample, though the example of introducing the electric stimulation into the living body sample is shown in this example.

The brain slice specimen, the tissue segment of the living thing and various culture specimens, etc. are exemplified as the living body sample.

SECOND EXAMPLE

The second example of the living body function measurement method according to the present invention will be explained referring to FIG. 3. This example is an example of the method of measuring the function for the visual stimulation in the brain of the animal.

Figure 3:
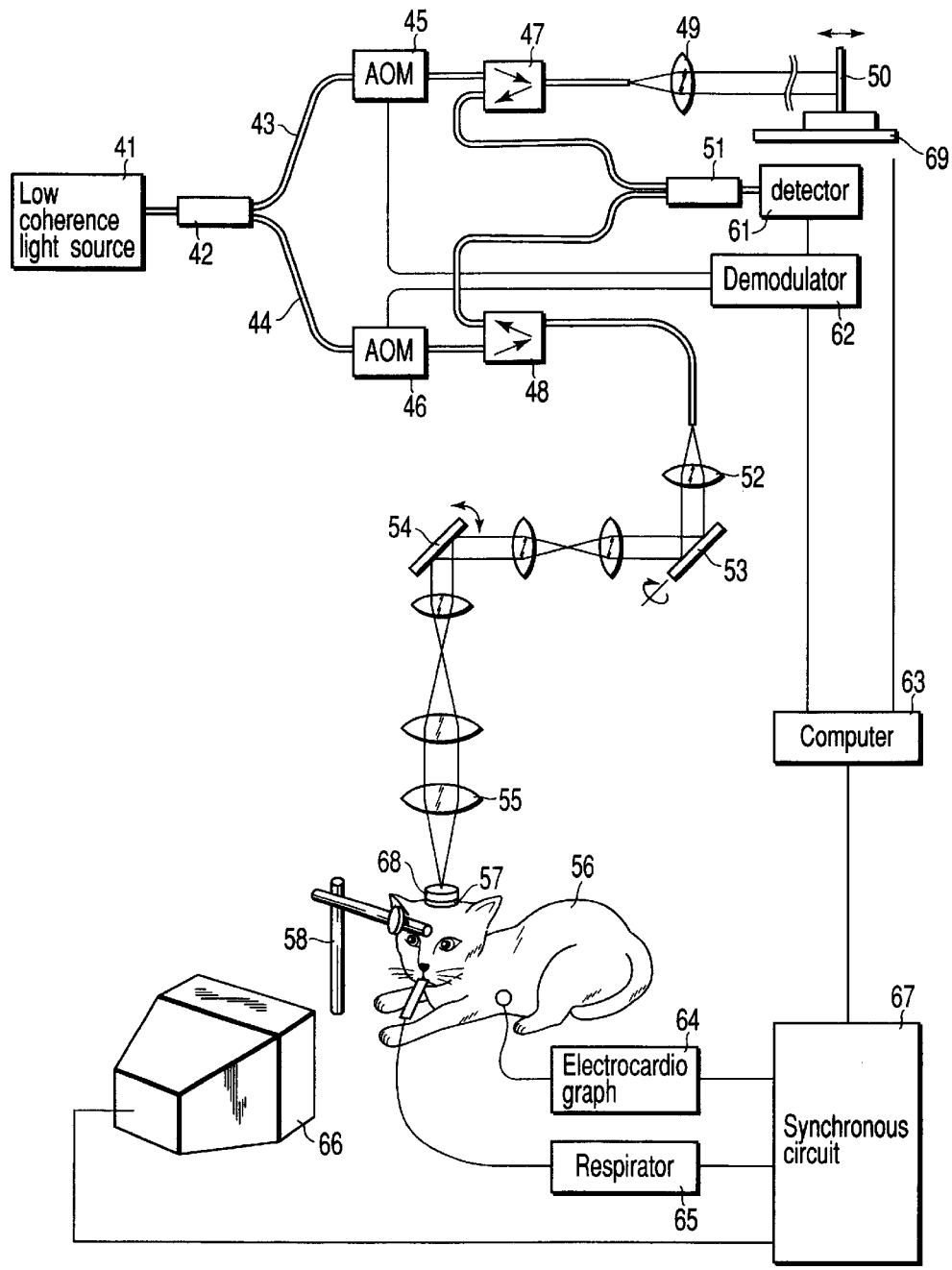
FIG. 3 is a figure, which shows a configuration to achieve a measurement method according to the second example of the present invention.

In FIG. 3, the light emitted from the low coherence light source 41 is led to the fiber coupler 42 through the optical fiber, and is separated into the reference optical path 43 and the signal optical path 44 by the fiber coupler 42. The light of the reference optical path 43 is reflected with the mirror 50 after passing through the AOM (Acousto-Optic Modulator) 45 and the circulator 47 and is emitted from the collimator lens 49. The light reflected by the mirror 50 reaches the fiber coupler 51 by passing the collimator lens 49 and the circulator 47. The light on the signal optical path 44 is emitted from the collimator lens 52 by passing through the AOM 46 and the circulator 48. The light emitted from the collimator lens 52 is reflected by the, galvanomirrors 53 and 54, and is irradiated to the observation area 57 of the living body sample 56 by the objective lens 55. The reflected light from the observation area 57 reaches the fiber coupler 51 by passing through the objective lens 55, the galvanomirrors 54 and 53, the collimator lens 52, and the circulator 48. The light on the reference optical path and the light on the signal optical path are synthesized by the fiber coupler 51, and are detected with the detector 61. The output of the detector 61 is input to the demodulator 62.

The output signal of the demodulator 62 is input to the computer 63.

The galvanomirrors 53 and 54 are used to scan the light irradiated by the objective lens 55 in the vertical direction to the optical axis of the objective lens. The distribution of the heterodyne interference signal in a vertical plane to an optical axis of the objective lens 55 can be observed by arranging the mirror 50 so that the length of the optical path of the signal optical path 44 and the reference optical path 43 are equal to. The distribution of the heterodyne interference signal in parallel plane to the optical axis of the objective lens 55 can be observed by scanning only either of the galvanomirror 53 or the galvanomirror 54, and scanning the mirror 50 by the scanning stage 69.

The AOM 45 and the AOM 46 are driven with a slightly different frequency. The demodulator 62 performs demodulation with a corresponding frequency to the difference frequency of the driving frequency of the AOM 45 and the AOM 46. The lock-inn amplifier etc. can be used as the demodulator 62. Though the AOMs are arranged on both optical paths in the embodiment, the AOM is arranged in one of optical paths and the modulator 62 may be perform modulation with the frequency corresponding to the one of modulated frequency thereof.

In this example, the cat is used as the living body sample 56 and the spatial patterns shown in FIG. 4A and FIG. 4B as a visual stimulation is shown to the cat. The spatial patterns which become the visual stimulation are displayed on the pattern display device 66. The observation area 57 is a visual area of the cerebral cortex of the cat. The observation window 68 to observe the observation area 57 is provided on the head of the cat. The head is fixed with the support 58 so that the position of the observation area 57 should not move to the objective lens 55. The electrocardiograph 64 and the respirator 65 are attached to the cat. The electrocardiograph 64 monitors the timing of the heartbeat, and outputs the signal to the synchronous circuit 67.

The synchronous circuit 67 controls the display timing of the pattern in a timing of the operation of the respirator 65 and the pattern display device 66. The operation of the synchronous circuit 67 is controlled with the computer 63. The operation timing of each equipment connected with the synchronous circuit 67 will be explained. FIG. 5A to FIG. 5F are figures showing the operation timing of each equipment. Each axis of abscissas indicates a time. FIG. 5A shows a request signal of the signal acquisition input to the synchronous circuit 67 by the computer 63. FIG. 5B shows an turning-on and -off control signal of the respirator 65. FIG. 5C shows the phase of the operation of the respirator 65. FIG. 5D shows an output signal of the electrocardiograph 64. FIG. 5E shows a signal acquisition start signal input from the synchronous circuit 67 to the computer 63. FIG. 5F shows an turning-on or -off control signal of the pattern display device 66.

In FIG. 5A, it is assumed that the request signal of the signal acquisition is input to the synchronous circuit 67 by the computer 63 at time t1.

After time t1, the synchronous circuit 67 detects a timing t2 that the phase signal of the operation of the respirator 65 rises (FIG. 5C). At this time, the operation of the respirator 65 temporarily becomes in the off state (FIG. 5B). After time t2, the synchronous circuit 67 detects a timing t3 of a first output signal from the electrocardiograph 64 (FIG. 5D). At this time, the synchronous circuit 67 changes the operation of the respirator 65 in the on state (FIG. 5B) and at the same time outputs the signal indicating the signal acquisition start to the computer 63 (FIG. 5E). The operation of the pattern display device 66 is started after passing a predetermined time T1 from time t3, and the spatial pattern is displayed only during time T2 (FIG. 5F). Therefore, at time t3, the computer 63 starts the signal acquisition in a state that the operation of the heart beat and breath are in phase. Therefore, the movement of the living body sample 56 can be arranged always thoroughly at each observation. After the heart beat and breath are in phase, the visual stimulation given to the living body sample can be controlled anytime with the constant timing. The spatial patterns of FIG. 4A and FIG. 4B are displayed as the visual stimulation according to the above-mentioned operation timing controlled by the synchronous circuit 67.

To observe the difference of the reaction in the observation area 57 before and after displaying the patterns, the difference of the observation signal can be calculated with the computer 63. The difference of the signal between different patterns can be calculated.

FIG. 6 is a figure, which shows a result of measuring the reaction for the visual stimulation which uses the spatial pattern with the above-mentioned device in part of sight-field of the cerebral cortex of the cat. Here, the distribution of the signal change along a depth directional of the objective lens is measured in the observation area 57 by, scanning only mirror 50 by the scanning stage 69f without operating the galvanomirrors 53 and 54. In FIG. 6, when the spatial pattern of FIG. 4A is shown to the cat, the real line shown by H is obtained as a result. When the spatial pattern of FIG. 4B is shown to the cat, the dotted line shown by V is obtained as a result. The result shown in FIG. 6 is the result that the difference between the heterodyne interference signal intensity when the spatial pattern is not shown and the heterodyne interference signal intensity when the spatial pattern is shown. The axis of abscissas of the graph indicates the position of the mirror 50, and the length of the optical path of the reference optical path 43 becomes long according to an increase of the numerical value. The position 0 of the axis of abscissas corresponds to the surface of the cerebral cortex and corresponds to a deep position according to an increase of the numerical value of the axis of abscissas corresponding to the surface of cerebral cortex. There is no difference in the reaction in both H and V from the surface of cerebral cortex in a shallow area as seen from FIG. 6. However, H and V are greatly different in the area where the numerical value of the axis of abscissas becomes more than 0.4. Therefore, it is confirmed that the reaction to the visual stimulation is different according to the difference of the given spatial pattern in this observation area.

Though the result of FIG. 6 is a result when the galvanomirror does not operate, it is possible to measure the depth distribution of the reaction for the stimulation by scanning in a vertical direction to the optical axis of the objective lens by operating the galvanomirror. Therefore, the living body function in three dimensions can be measured.

The reaction when the stimulations for the sensory organs other than the sight, for example, such as aural of the living body sample, sense of smell, and the taste are given can be observed, though the example of observing the reaction when the visual stimulation is given to the living body sample is shown in this example.

The living body function measurement method according to the present invention is characterized by comprising: separating a light from a low coherence light source into a signal light and a reference light; modulating a frequency of at least one of the signal light and the reference light; irradiating the signal light to an observation area of a living body sample; giving a stimulation to the living body sample from an outside of the living body sample; synthesizing the signal light via the observation area and the reference light and detecting a heterodyne interference signal; and measuring a living body function of the observation area by measuring a change in the heterodyne interference signal when the stimulation is changed.

The preferred manners of the present invention are as follows.

The following manners may be applied solely or applied by combining them.

(1) A difference of an intensity of the heterodyne interference signal is measured before and after changing the stimulation.

(2) A time response for the stimulation in the observation area is measured by measuring a time change of the heterodyne interference signal.

(3) The stimulation is given in synchronous with a movement of the living body sample according to an activity of the living body sample.

(4) The heterodyne interference signal is measured in synchronous with a movement of the living body sample according to an activity of the living body sample.

(5) In (3) or (4), the activity is breath or beat in the living body sample.

In the observation in an in vivo check, the living body sample relatively moves to the measurement device by breath and beat. The position of the observation area changes and it becomes difficult to detect an accurate reaction by moving the living body sample during observation. In the above-mentioned embodiment, since the observation is performed in synchronous with the activity by monitoring an activity such as breath and beat of the living body, the influence such as the vibrations of the sample according to an activity of the living body can be removed.

(6) The observation area is a part of a brain of the living body sample.

(7) The stimulation is given to a sensory organ of the living body sample.

(8) The stimulation is a visual stimulation and is an image pattern projected to a retina of the living body sample.

(9) The stimulation is a stimulation with an the electric stimulation or a medicine.

(10) The heterodyne interference signal is measured in synchronous with the movement of the living body sample according to an activity of the living body sample.

(11) The observation area is a part of a brain of said living body sample and the stimulation is given to a sensory organ of said living body sample.

As mentioned above, the living body function of the observation area can be observed in the high-resolution evaluation in the living body by measuring the change in the heterodyne interference signal when light from the low coherence light source is irradiated to the observation area of the living body sample, and the stimulation given to the living body sample is changed according to the above-mentioned embodiment.

What is claimed is:

1. A living body function measurement method comprising:

separating a light from a low coherence light source into a signal light and a reference light;

modulating a frequency of at least one of the signal light and the reference light;

irradiating the signal light to an observation area of a living body sample in vivo;

giving a stimulation to the living body sample from an outside of the living body sample;

synthesizing the signal light via the observation area and the reference light and detecting a heterodyne interference signal; and measuring a living body function of the observation area by measuring a change in the heterodyne interference signal when the stimulation is changed.

2. The living body function measurement method according to claim 1, wherein a difference of an intensity of the heterodyne interference signal is measured before and after changing the stimulation.

3. The living body function measurement method according to claim 2, wherein the heterodyne interference signal is measured in synchronous with a movement of the living body sample according to an activity of the living body sampler.

4. The living body function measurement method according to claim 2, wherein a time response for the stimulation in the observation area is measured by measuring a time change of the heterodyne interference signal.

5. The living body function measurement method according to claim 2, wherein the heterodyne interference signal is measured in synchronous with a movement of the living body sample according to an activity of the living body sample.

6. The living body function measurement method according to claim 1, wherein a time response for the stimulation in the observation area is measured by measuring a time change of the heterodyne interference signal.

7. The living body function measurement method according to claim 6, wherein the heterodyne interference signal is measured in synchronous with the movement of the living body sample according to an activity of the living body sample.

8. The living body function measurement method according to claim 6, wherein the stimulation is given in synchronous with a movement of the living body sample according to an activity of the living body sample.

9. The living body function measurement method according to claim 1, wherein the stimulation is given in synchronous with a movement of the living body sample according to an activity of the living body sample.

10. The living body function measurement method according to claim 9, wherein the heterodyne interference signal is measured in synchronous with a movement of the living body sample according to an activity of the living body sample.

11. The living body function measurement method according to claim 1, wherein the heterodyne interference signal is measured in synchronous with a movement of the living body sample according to an activity of the living body sample.

12. The living body function measurement method according to claim 11, wherein the activity is breath or beat in the living body sample.

13. The living body function measurement method according to claim 12, wherein the observation area is a part of a brain of said living body sample and the stimulation is given to a sensory organ of said living body sample.

14. The living body function measurement method according to claim 1, wherein the observation area is a part of a brain of the living body sample.

15. The living body function measurement method according to claim 1, wherein the stimulation is given to a sensory organ of the living body sample.

16. The living body function measurement method according to claim 15, wherein the stimulation is a visual stimulation and is an image pattern projected to a retina of the living body sample.

17. The living body function measurement method according to claim 1, the stimulation is a stimulation with an the electric stimulation or a medicine.

* * * * *